United States Patent [19]

Forbriger, Jr.

[11] 4,349,537

[45] Sep. 14, 1982

[54] PERMANENT WAVE NEUTRALIZER

[75] Inventor: Arthur W. Forbriger, Jr., Cincinnati, Ohio

[73] Assignee: Tressa, Inc., Cincinnati, Ohio

[21] Appl. No.: 245,959

[22] Filed: Mar. 20, 1981

[51] Int. Cl.$^3$ .......................... A61K 7/09; A61K 7/11
[52] U.S. Cl. ........................................ 424/71; 424/72
[58] Field of Search .............................. 424/71, 72, 70

[56] References Cited

U.S. PATENT DOCUMENTS 2,540,494 2/1951 Schwarz ................................ 424/72
2,780,579 2/1957 Schwarz et al. .................. 424/71 X
3,109,778 11/1963 Shansky et al. ....................... 424/72

Primary Examiner—Donald B. Moyer
Attorney, Agent, or Firm—Wood, Herron & Evans

[57] ABSTRACT

This invention relates to a new permanent wave neutralizer and a method for permanently waving and styling hair. The permanent wave neutralizer contains a sufficient amount of citric acid and optionally a salt of citric acid so as to provide a molar concentration of citric ion of at least 0.2 and a pH of between 1.9 and 4.0.

5 Claims, No Drawings

PERMANENT WAVE NEUTRALIZER

BACKGROUND OF THE INVENTION

The prior art is replete with various methods and solutions for permanently waving and styling hair. In one commonly employed type of permanent waving, hair is wrapped around rods and a basic solution of thioglycolic acid is applied to reduce the keratin in the hair. Thereafter the hair is removed from the rods, the solution rinsed from the hair with water and a setting or a neutralizing and oxidizing solution is applied to the hair. This neutralizing and oxidizing solution frequently consists of hydrogen peroxide. The purpose of this solution is to oxidize the keratin and restore the strength of the hair and set the hair. One such process is disclosed in my U.S. Pat. No. 3,399,683 granted Sept. 3, 1968.

The above described processes are well known and have been employed for many years. Various attempts have been made through the addition of various chemical compounds to the reducing or oxidizing solution or through the use of extremely different oxidizing or reducing solutions to provide improved cold waving processes. For example, U.S. Pat. Nos. 2,403,937, 3,555,147, 3,865,930 and 3,071,515 disclose the inclusion of citric acid in cold permanent waving processes.

It has been the principal objective of this invention to improve upon the prior art permanent waving process and more particularly to provide a stronger better defined wave pattern while at the same time eliminating random fly-away appearance of the hair after drying.

SUMMARY OF THE INVENTION

It has been unexpectedly discovered that a very strong, well defined hair wave pattern can be obtained and that random fly-away appearance can be eliminated if a precise amount of citrate ion is provided in the neutralizer and oxidizing solution and if that neutralizing and oxidizing solution has a pH of 2.0 to 4.0, made acidic by citric acid. It has also been empirically determined that the neutralization and oxidizing step is most effectively carried out with the hair wound on the rods and with the hair being subjected to a heating step.

In the oxidizing and neutralizing solution of the present invention a suitable oxidizing agent such as hydrogen peroxide is included in conventional amounts, for example, about 1% to 4% by weight. Other conventional materials such as fragrances, etc. may be included in aqueous solution with the oxidizing agent.

The neutralizing and oxidizing solution of the present invention may be utilized after a conventional keratin reducing agent has been applied to the hair such as ammonium thioglycolate. The present neutralizing and oxidizing solution may also be applied following the use of other conventional keratin reducing agents.

DESCRIPTION OF THE PREFERRED EMBODIMENTS

It has been unexpectedly discovered that improved results can be obtained if the oxidizing and neutralizing solution includes a specified amount of citrate ion in solution and if the oxidizing and neutralizing solution is rendered acidic, i.e., pH 2–4, through the use of citric acid. While citric acid has been utilized in cold permanent waving solutions before, it has not been employed in a neutralizing and oxidizing solution in the amounts discovered by this inventor to be required in order to provide the superior results. More particularly, applicant has discovered that the advantages of the present invention can only be obtained when the oxidizing and neutralizer solution has been made acidic, i.e., pH 1.9–4, through the use of citric acid and only when there is present a molar concentration of citrate ion of at least 0.2. In contrast to this pH range and this molar concentration the prior art as typified by U.S. Pat. No. 3,071,515 only discloses using about 1.4% citric acid which does not provide the pH and molar concentration of citrate ion which have been found to be required in order to provide the superior results of the present invention.

The required level of citrate ion can be provided through the use of citric acid by itself. A level of about 4.0% citric acid is required in a neutralizer containing about 1.3% hydrogen peroxide. It has been discovered that an especially effective combination is provided if sodium citrate dihydrate is employed in combination with the citric acid. Especially desirable results can be obtained through a combination of about 3.0% citric acid and about 2.5% sodium citrate dihydrate. Through the use of such a combination a pH of about 3.8 and a molar concentrate of 0.21 are obtained.

As noted the neutralizing and oxidizing solution of the present invention as compared to a formulation which includes about 1.5% citric acid which is outside the scope of the present invention provides a finished curl where the curl is very well defined and where random fly-away appearance has been substantially or completely eliminated.

An especially effective way of treating hair with the neutralizing and oxidizing solution of the present invention, is to treat the hair with the solution while the hair is wound on rods and while in such a state the solution is dried by the application of heat.

In order to test the effectiveness of the present neutralizing and oxidizing solution in contrast to an oxidizing and neutralizing solution which did not contain the required level of citrate ion concentration and the required pH, the following tests were performed. In all tests the following permanent wave solution was utilized.

| Permanent Wave Solution | % by wt. |
| --- | --- |
| Ammonium Thioglycolate (60% Thio Acid) | 11.7 |
| Aqua Ammonia (29% Ammonia) | 4.2 |
| Polyethylene glycol (23) ether of lauryl alcohol | 0.6 |
| Propylene Glycol | 0.6 |
| Hydrolyzed Animal Protein (50%) | 0.8 |
| Styrene/Acrylate Copolymer Latex (40%) | 0.5 |
| Fragrance | 0.2 |
| Pentasodium diethylene triamine penta acetate (40%) | 0.1 |
| Deionized water | 81.3 |
| | 100.0 |

Table I sets out the various neutralizer solutions which were tested. Examples 5, 6 and 7 are examples of the present invention while Examples 1, 2, 3, 4 and 8 illustrate molar concentrations of citrate ion and/or pH outside of the scope of the present invention which demonstrate that the advantageous results of the present invention can only be achieved through the use of a solution which contains a molar concentration of citrate ion of at least 0.2 and a pH of between about 2 and 4. In testing the solutions set forth in Table I, the following procedures and results were obtained.

Sample tresses prepared from twenty-five (25) hairs glued together at the root end were wound on a special mandrel made from ¼" diameter Lucite plastic rod. The mandrel contained a helical groove at six (6) threads/inch. This provided a one inch (1") of thread or six (6) revolutions. After the tress was wound around the Lucite rod it was secured at each end with a small piece of rubber tubing. After so winding the tress, it was immersed in the permanent waving solution described above for ten (10) minutes. Thereafter it was rinsed by dipping in a beaker (150 ml.) of tepid water fifty (50) times and then immersed in the particular neutralizer tested for a period of five (5) minutes. The tress was then removed from the rod and rinsed by dipping in tepid water (150 ml.) fifty (50) times. It was then suspended vertically from the glued end and allowed to dry at ambient temperature. A number of measurements were made on the suspended tress both while it was wet and after it was dried. For example, the vertical length of the tress was measured, the distance between wave crests and the total degree rotation, i.e., the number of turns times 360 were determined. After the tress had dried the appearance of it was noted. More particularly the tress was studied in terms of the ability of the solution to impart dry wave uniformity, the ability to provide a strong defined wave pattern, and the ability to eliminate random fly-away appearance of the hair. Substantial and significant differences were noted between the use of the examples the present invention, i.e., 5, 6 and 7, in contrast to the other noninventive examples. More particularly, it was quite apparent that the examples of the present invention provide a much stronger and better defined wave pattern. Random fly-away appearance after drying was substantially, if not completely, eliminated. No significant differences were noted between Example 2 which contained 1.5% citric acid and Example 1 which contained no citric acid. The differences between Example 5 and Example 2 and 1 on the other hand were quite apparent. Example 5 showed substantially improved uniformity, the wave was much stronger and better defined, and there was no fly-away appearance. Example 8 which did contain a molar concentration of citrate ion within the scope of the present invention, but which did not however have a pH of 2-4, did not exhibit the improved results obtained through the use of Examples 5, 6 or 7.

A modified procedure was employed which utilized the solution of Example 5. The above described procedure was modified in the following way. After the neutralizer was applied to the wrapped tress it was dried on the rod for five (5) minutes through the use of a hot air dryer. Improved results in terms of the defined wave pattern and its strength were obtained.

TABLE I

| | | EXAMPLE | | | | | | | |
|---|---|---|---|---|---|---|---|---|---|
| | | 1 | 2 | 3 | 4 | 5 | 6 | 7 | 8 |
| Neutralizer Solutions | | | | | | | | | |
| Hydrogen Peroxide (35%) | | 3.75 | 3.75 | 3.75 | 3.75 | 3.75 | 3.75 | 3.75 | 3.75 |
| Isostearamido propylmorpholine lactate (25%) | | 0.75 | 0.75 | 0.75 | 0.75 | 0.75 | 0.75 | 0.75 | 0.75 |
| Cetearyl alcohol/ceteth-20 | | 0.50 | 0.50 | 0.50 | 0.50 | 0.50 | 0.50 | 0.50 | 0.50 |
| Mineral Oil | | 0.07 | 0.07 | 0.07 | 0.07 | 0.07 | 0.07 | 0.07 | 0.07 |
| Methyl parahydroxy benzoate | | 0.10 | 0.10 | 0.10 | 0.10 | 0.10 | 0.10 | 0.10 | 0.10 |
| Phenacetin | | 0.10 | 0.10 | 0.10 | 0.10 | 0.10 | 0.10 | 0.10 | 0.10 |
| Fragrance | | 0.05 | 0.05 | 0.05 | 0.05 | 0.05 | 0.05 | 0.05 | 0.05 |
| Citric Acid | | 0 | 1.5 | 2.0 | 3.0 | 4.0 | 6.0 | 3.0 | 1.33 |
| Sodium Citrate Dihydrate | | 0 | 0 | 0 | 0 | 0 | 0 | 2.5 | 5.0 |
| Deionized water | qs. | 100.00 | 0 | 0 | 0 | 0 | 0 | 0 | 0 |
| pH | | 3.3 | 2.2 | 2.15 | 2.0 | 1.90 | 1.9 | 3.8 | 5.0 |
| Molar Concentration Of Citrate Ion | | 0 | 0.08 | 0.10 | 0.16 | 0.21 | 0.31 | 0.24 | 0.24 |

Having thus described my invention, I claim:

1. A permanent waving neutralizer and oxidizing solution consisting essentially of an aqueous solution containing at least 0.2 molar citrate ion and having a sufficient amount of citric acid to provide a pH of about 1.9 to 4, and an oxidizing agent.

2. The solution of claim 1 wherein the citrate ion concentration and the pH of the solution is obtained by a mixture of citric acid and sodium citrate dihydrate.

3. The solution of claim 1 wherein the citrate ion concentration and the pH is obtained through the use of citric acid.

4. The solution of claim 1 wherein the oxidizing agent is hydrogen peroxide.

5. The solution of claim 4 wherein the solution includes citric acid and sodium citrate dihydrate.

* * * * *